United States Patent
Taylor

(10) Patent No.: US 10,034,752 B2
(45) Date of Patent: Jul. 31, 2018

(54) METHOD OF IMPLANTING A PENILE PROSTHETIC BY CAPTURING A SUTURE IN A SLOT FORMED THROUGH AN EXTERIOR SURFACE OF A NEEDLE

(71) Applicant: Coloplast A/S, Humlebaek (DK)

(72) Inventor: Jeffrey Brian Taylor, Forest Lake, MN (US)

(73) Assignee: Coloplast A/S, Humlebaek (DK)

( * ) Notice: Subject to any disclaimer, the term of this patent is extended or adjusted under 35 U.S.C. 154(b) by 458 days.

(21) Appl. No.: 14/698,866

(22) Filed: Apr. 29, 2015

(65) Prior Publication Data

US 2016/0317306 A1    Nov. 3, 2016

(51) Int. Cl.
*A61F 2/26* (2006.01)
*A61B 17/04* (2006.01)

(52) U.S. Cl.
CPC ............ *A61F 2/26* (2013.01); *A61B 17/0469* (2013.01)

(58) Field of Classification Search
CPC ........................................................ A61F 2/26
USPC ..................................................... 600/38–41
See application file for complete search history.

(56) References Cited

U.S. PATENT DOCUMENTS

| | | | |
|---|---|---|---|
| 4,244,370 A * | 1/1981 | Furlow | A61B 17/04 128/DIG. 20 |
| 5,433,722 A * | 7/1995 | Sharpe | A61B 17/0469 606/139 |
| 5,868,729 A * | 2/1999 | Pelfrey | A61F 2/26 600/38 |
| 5,904,692 A * | 5/1999 | Steckel | A61B 17/0469 128/898 |
| 5,993,459 A | 11/1999 | Larsen et al. | |
| D449,691 S | 10/2001 | Reiley et al. | |
| D482,787 S | 11/2003 | Reiss | |
| D505,200 S | 5/2005 | Simpson et al. | |
| D539,900 S | 4/2007 | Fedenia et al. | |
| 7,407,482 B2 | 8/2008 | Kuyava | |
| D607,102 S | 12/2009 | Robinson | |
| D610,258 S | 2/2010 | Robinson | |
| 8,066,718 B2 * | 11/2011 | Weisel | A61B 17/06109 606/139 |
| D663,838 S | 7/2012 | Mastri et al. | |
| D667,954 S | 9/2012 | Mastri et al. | |
| D673,670 S | 1/2013 | Linnenschmidt | |
| D675,317 S | 1/2013 | Baxter et al. | |
| D678,511 S | 3/2013 | Fojtik | |
| D697,207 S | 1/2014 | Paget et al. | |
| D707,356 S | 6/2014 | Vonck et al. | |
| D708,738 S | 7/2014 | Berman et al. | |

(Continued)

*Primary Examiner* — Samuel Gilbert
(74) *Attorney, Agent, or Firm* — Coloplast Corp., Coloplast A/S; Nick Baumann

(57) ABSTRACT

One aspect provides advancing a distal end of a needle out of a bore of a tool, and capturing a suture in a slot formed through an exterior surface of the needle, with the suture engaged with a penile implant. The method includes retracting the distal end of the needle and a portion of the suture into the bore of the tool, and inserting a shaft of the tool into a corpora cavernosum of a penis and forcing the distal end of the needle and the portion of the suture out of the bore of the tool and through a glans of the penis. The method includes retracting the needle into the bore and retaining the portion of the suture exterior to the glans of the penis. Pulling on the suture pulls the penile implant into the corpora cavernosum of the penis.

13 Claims, 17 Drawing Sheets

(56) References Cited

U.S. PATENT DOCUMENTS

| | | |
|---|---|---|
| D715,431 S | 10/2014 | Vonck et al. |
| D734,459 S | 7/2015 | Arnett |
| D748,775 S | 2/2016 | Greeson, Jr. |
| 9,451,982 B1 | 9/2016 | Taylor |
| 2004/0133211 A1 | 7/2004 | Raskin et al. |
| 2016/0317306 A1 | 11/2016 | Taylor |

* cited by examiner

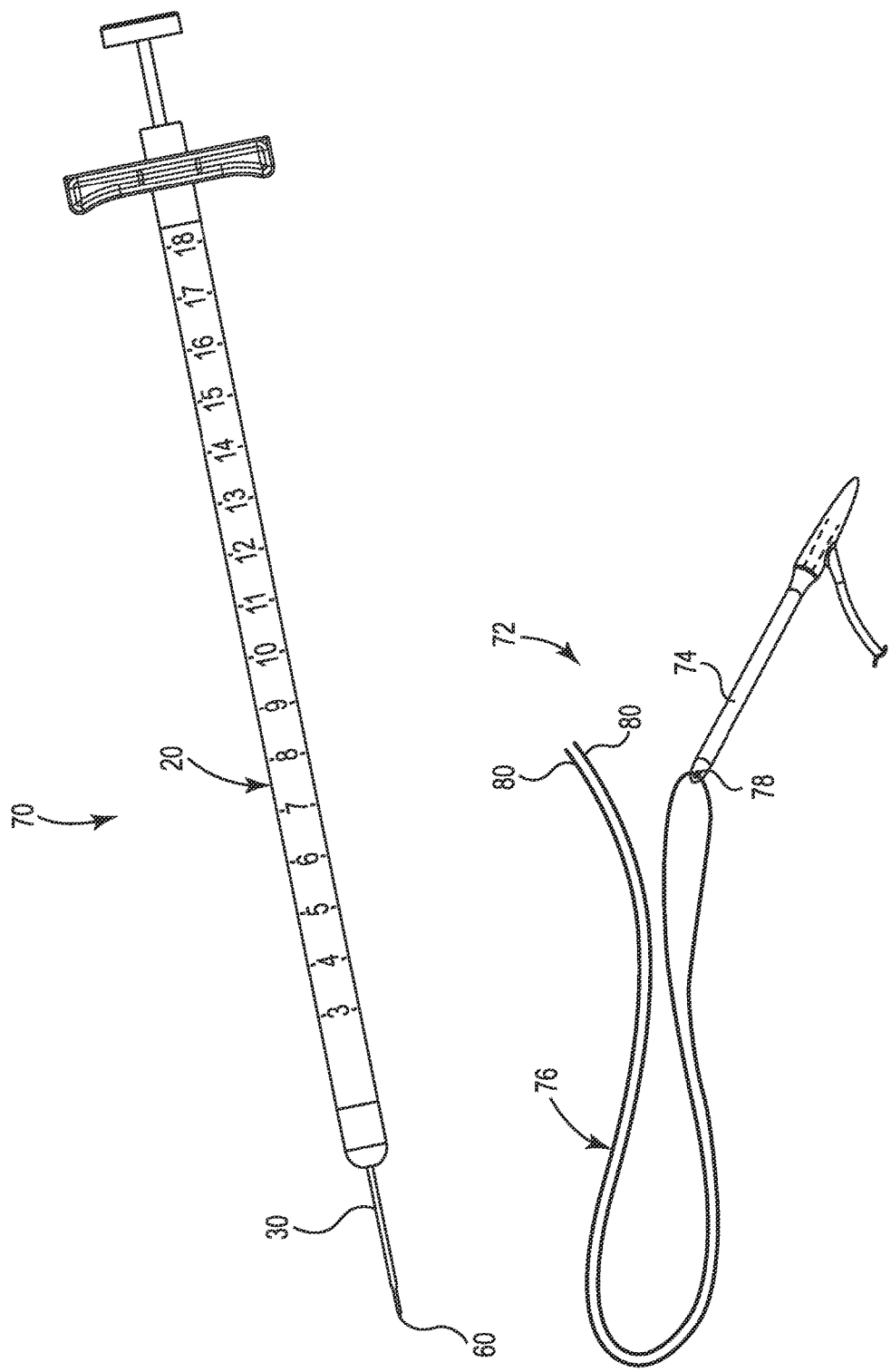

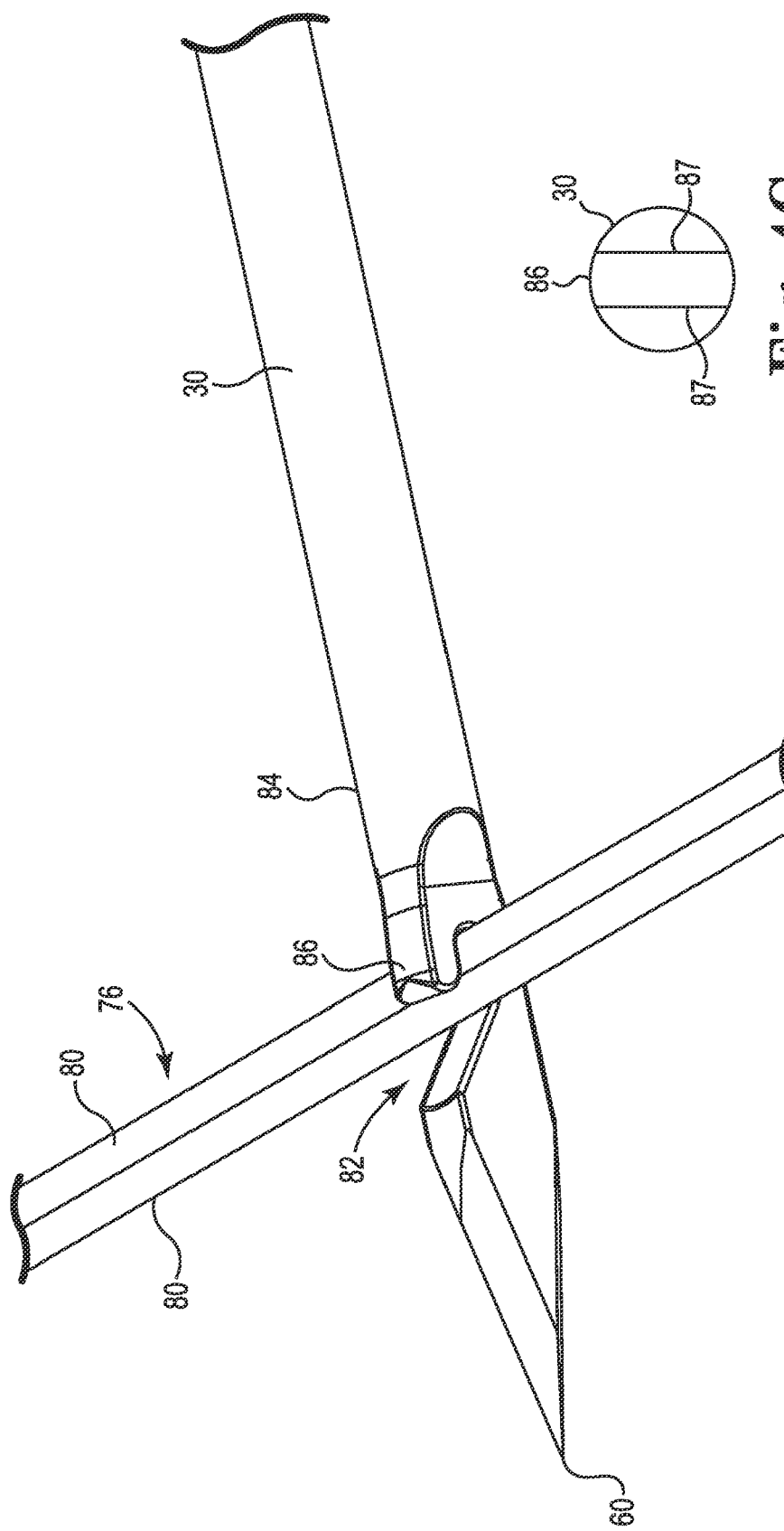

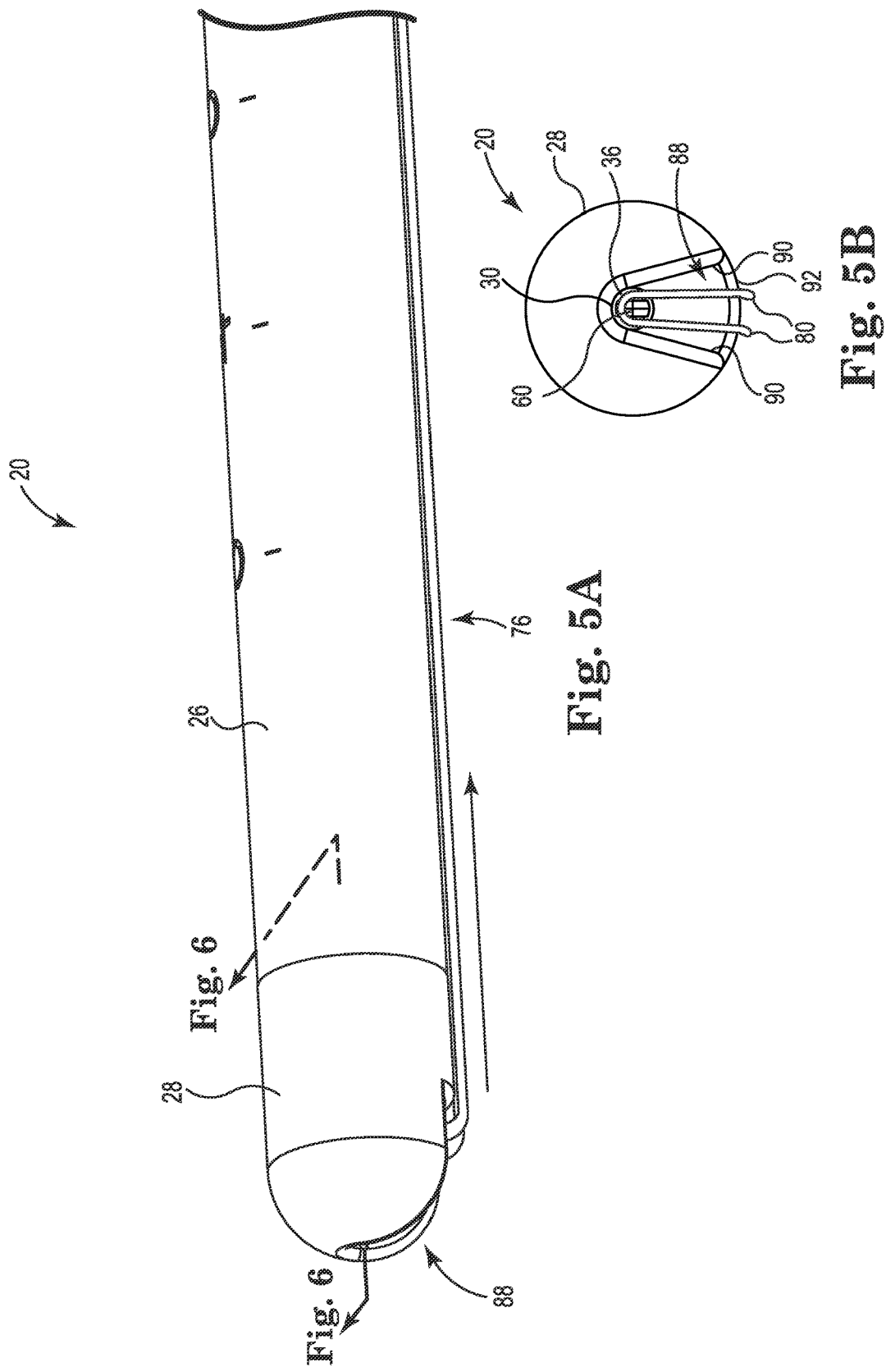

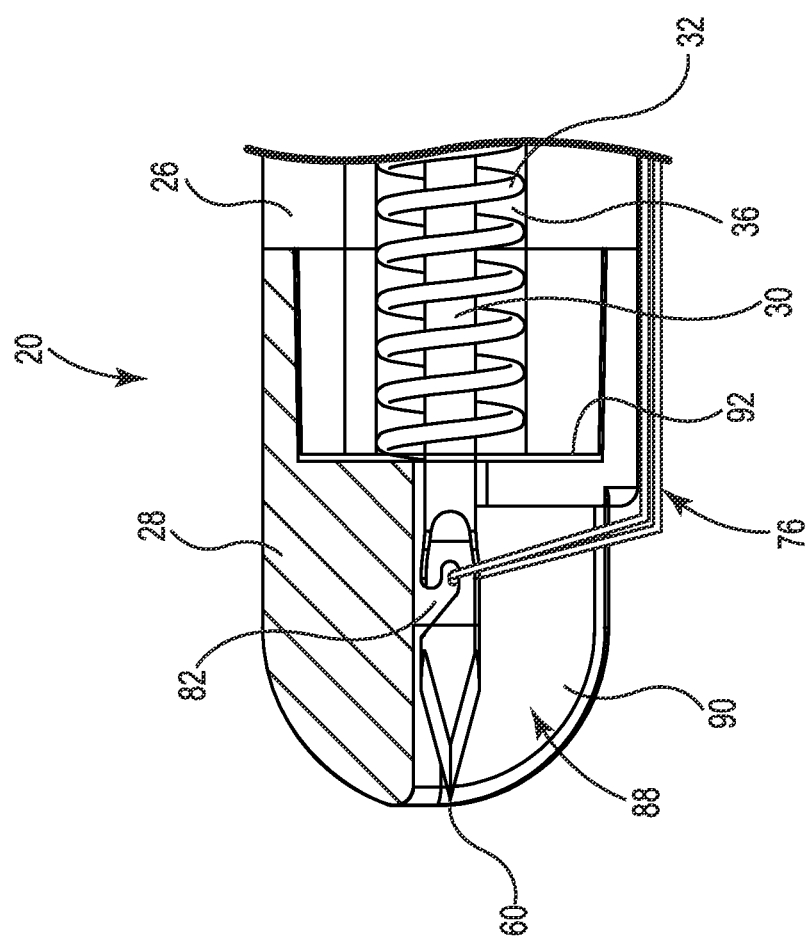

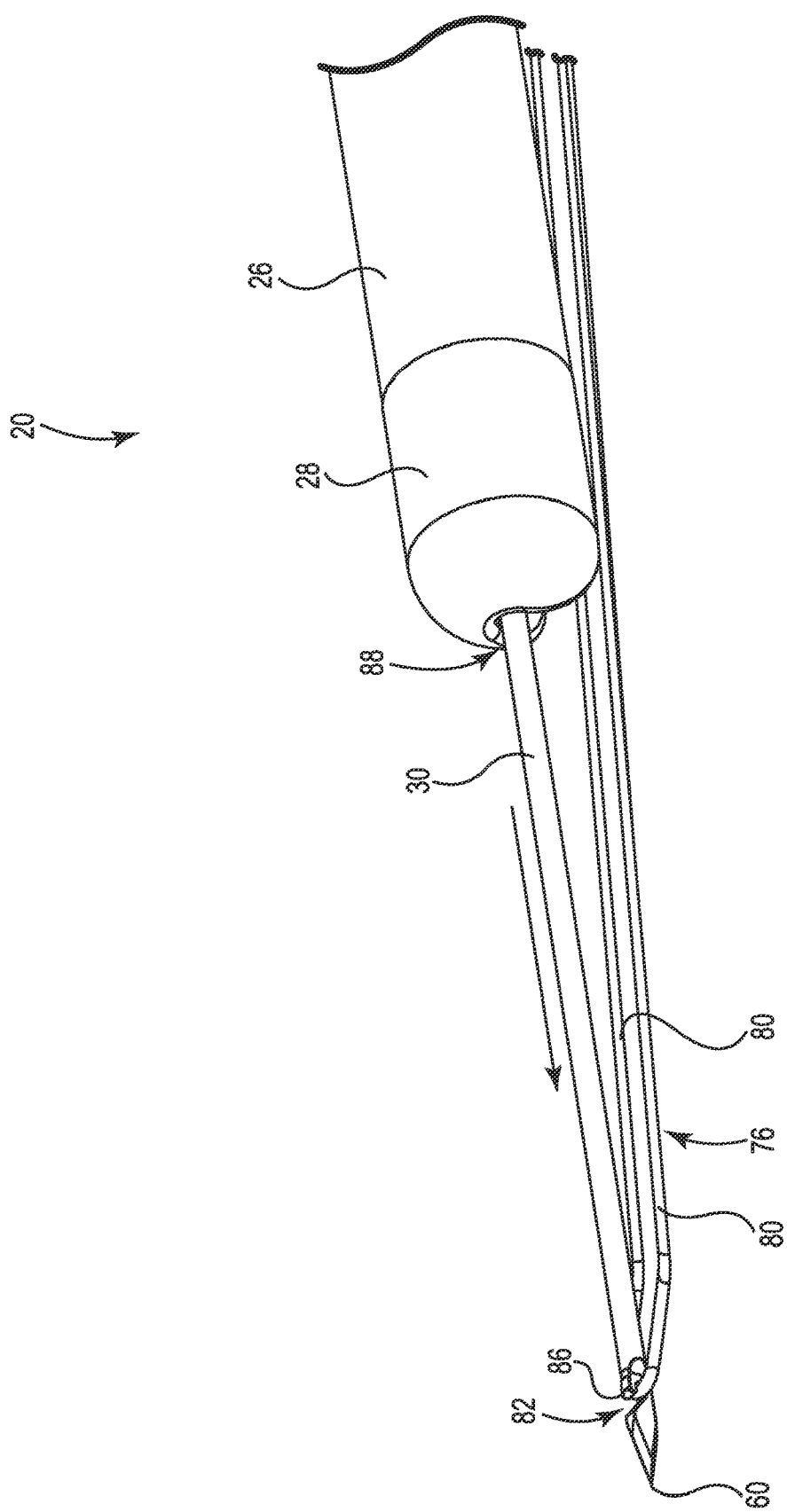

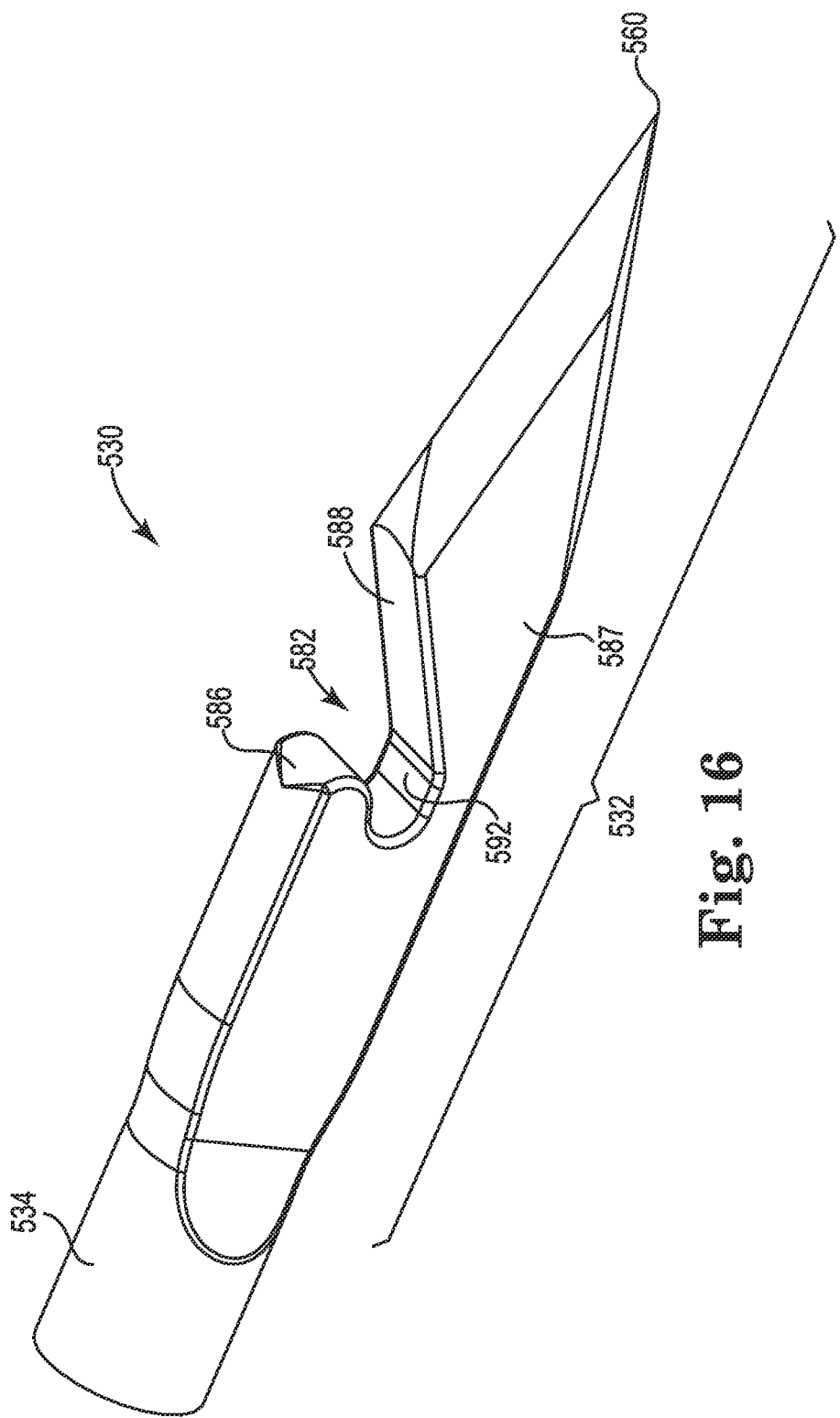

METHOD OF IMPLANTING A PENILE PROSTHETIC BY CAPTURING A SUTURE IN A SLOT FORMED THROUGH AN EXTERIOR SURFACE OF A NEEDLE

CROSS-REFERENCE TO RELATED APPLICATIONS

This non-provisional application having Ser. No. 14/698,866 is filed on Apr. 29, 2015 and incorporates by reference the entirety of three design patent applications filed on the same day. This non-provisional application incorporates by reference the entirety of those three design patent applications, each titled SURGICAL TOOL, each invented by Jeffrey Brian Taylor, each filed on Apr. 29, 2015 and having Ser. Nos. 29/525,331; 29/525,332; and 29/525,333.

SUMMARY

One aspect provides a method of implanting a penile prosthetic. The method includes advancing a distal end of a needle out of a bore of a tool and capturing a suture in a slot formed through an exterior surface of the needle, with the suture engaged with a penile implant. The method includes retracting the distal end of the needle and a portion of the suture into the bore of the tool, inserting a shaft of the tool into a corpora cavernosum of a penis, and forcing the distal end of the needle and the portion of the suture out of the bore of the tool and through a glans of the penis. The method includes retracting the distal end of the needle into the bore of the tool and retaining the portion of the suture exterior to the glans of the penis. The method includes removing the shaft of the tool from the corpora cavernosum of the penis, pulling on the suture, and pulling the penile implant into the corpora cavernosum of the penis.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 3 is a perspective view of one embodiment of a system including the tool illustrated in FIG. 2 and a suture engaged with a penile implant.

FIG. 4A and FIG. 4B are perspective views of an exposed needle of the tool engaged with the suture illustrated in FIG. 3.

FIG. 4C is a front view of the needle.

FIG. 5A is a perspective view and FIG. 5B is an end view of the needle and the suture illustrated in FIG. 4A retracted to an unexposed position within the tool.

FIG. 6 is a longitudinal cross-sectional view of the distal end portion of the tool relative to the illustration of FIG. 5A.

FIG. 7 is a perspective view of one embodiment of the needle and a portion of the suture advanced out of an end of the tool.

FIG. 16 is a perspective view of one embodiment of a needle of the tool illustrated in FIG. 2.

DETAILED DESCRIPTION

Figure 1:
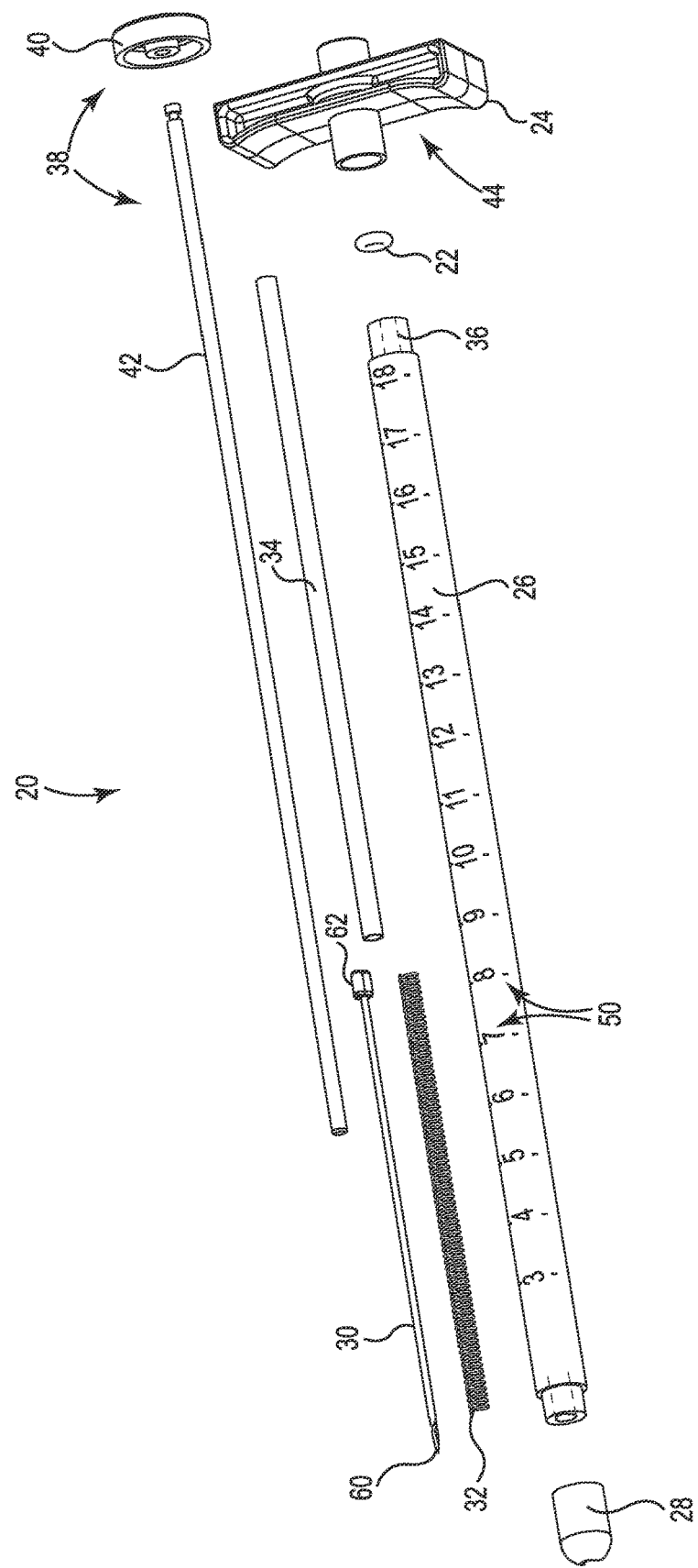
FIG. 1 is a perspective view of one embodiment of a schematic of disassembled components of a tool, where the tool is useful in implanting a penile prosthetic.

In the following detailed description, reference is made to the accompanying drawings. The drawings form a part of this specification and illustrate exemplary embodiments for practicing the invention. Directional terminology, such as "top," "bottom," "front," "back," "leading," "trailing," etc., is used with reference to the orientation of the Figure(s) being described. Because components of embodiments can be positioned in a number of orientations, the directional terminology is used for purposes of illustration and is in no way limiting. It is to be understood that other embodiments may be utilized and structural or logical changes may be made without departing from the scope of the invention. The detailed description describes examples for practicing the invention and is not to be read to limit the scope of the invention. The scope of the invention is defined by the attached claims.

Embodiments, and features of the various exemplary embodiments disclosed in this application, may be combined with each other ("mixed and matched"), unless specifically noted otherwise.

End means endmost. Relative to an observer, for example a surgeon, a distal end is the furthest endmost location of a distal portion of a thing being described, whereas a proximal end is the nearest endmost location of a proximal portion of the thing being described. The portion next to or adjacent to an end is an end portion.

An implanted penile prosthetic has proven useful in treating erectile dysfunction in men. One acceptable implantable penile prosthetic includes two inflatable cylinders implanted in the penis, a pump implanted in the scrotum or other internal space of the body, and a liquid holding reservoir implanted in the abdomen or other internal space of the body.

In a typical implantation procedure, the penis of the patient is incised in a corporotomy to expose a pair of corpora cavernosa that are aligned axially in a side-by-side orientation within the penis. A cutting implement, such as a curved Mayo scissors, is employed to penetrate the fascia of the penis and form an opening accessing each corpora cavernosum. Subsequently, each corpora cavernosum is dilated (opened) with an appropriate dilation tool to form a recess that is sized to receive one of the two cylinders of the penile prosthetic. Thereafter, a tool (referred to by surgical practitioners as a "Furlow" introducer) is inserted into each dilated corpora cavernosum to measure a length of the penis distally and proximally to determine a desired length of the cylinders to be implanted. A cylinder of the appropriately selected length is secured to a suture, and the suture is secured to a needle (sometimes called a "Keith" needle). The Keith needle is inserted into a bore of the Furlow introducer. The Keith needle could possibly fall out of the bore of the Furlow introducer, so the surgical staff handles the tool with care. The surgeon steadies the Furlow introducer with one hand and pushes a plunger (or obturator) of the Furlow introducer with the other hand to push the needle out of the bore. Pushing the plunger pushes the needle distally from of the introducer, through tissue of the penis, and out the glans penis. The exposed portion of the needle is handled by the surgeon. The needle is advanced out of the glans penis, the suture is removed from the needle, and the needle is discarded. The remaining suture is subsequently employed to tow the cylinder from the incision into the glans penis within the dilated corpora cavernosum.

The above-described procedure has proven effective when implanting penile prostheses. However, surgeons would appreciate having fewer parts to handle during the procedure and would welcome a tool that reduces or eliminates exposure to the sharp end of the Keith needle.

Embodiments provide a tool for measuring a length of the penis distally (forward toward the glans) and proximally (rearward toward the crus) to determine a suitable length for the implantable prosthetics.

Embodiments provide a tool with additional functionality over a Furlow introducer. Specifically, the tool is capable of both ejecting the needle forward through tissue and retrieving the needle backward into a bore of the tool. Retraction of the needle into the bore of the tool could potentially reduce exposure of the staff to the sharp end of the Keith needle.

Embodiments provide a needle that is secured to the tool and biased to move into and out of the bore of the tool to reduce the possibility of the needle undesirably falling away from the tool. Needles that fall out of the tool can become non-sterile if the needle leaves the sterile field and can possibly lead to an undesirable increased risk of needle sticks.

FIG. 1 is a perspective view of one embodiment of a schematic illustrating disassembled components of a tool 20. When assembled, the tool 20 is useful for introducing an implant into a penis.

The tool 20 includes an o-ring 22 that is located between a handle 24 and a shaft 26, a distal tip 28 that forms a distal end of the shaft 26, a needle 30, a spring 32, a needle stopper 34 that is retained in a bore 36 of the shaft 26, and a plunger assembly 38 including a button 40 attached to a rod 42. The rod 42 is insertable through the handle 24 and into the bore 36 of the shaft 26 and is operable to move a sharp point of the needle 30 outward from and back into the tip 28 of the tool 20.

The o-ring 22 is suitably fabricated from an elastomeric material and is located between the handle 24 and the shaft 26 to seal and provide a guide for the rod 42.

The handle 24 includes a curvature 44 that accommodates the fingers when the tool 20 is held in a hand. The button 40 is sized to matchup with the thumb when the fingers cradle the curvature 44 of the handle 24.

The shaft 26 is provided with indicia 50 printed or etched or marked on at least one side surface of the shaft 26 to indicate a length extending away from the distal end of the distal tip 28. In one embodiment, the indicia 50 are marked on multiple side surfaces of the shaft 26 for convenient viewing at any angle. The tool 20 is preferably disposable, so one suitable material for the shaft 26 includes a polymer such as an extruded polycarbonate or polypropylene or other high performance, low cost plastic material. In one embodiment, the indicia 50 measure centimeters a distance away from the end of the distal tip 28, which allows the surgeon to measure the length of the corpora cavernosum and select an appropriately sized penile prosthetic. The distal tip 28 is attached to the shaft 26 and is provided with an opening to allow the needle 30 to be exposed out of the shaft 26 when the plunger assembly 38 is moved in a distal direction.

The needle 30 includes a pointed distal end 60 opposite from a head 62. The spring 32 is sized to be positioned coaxial on the needle 30 between the pointed distal end 60 and the head 62. The rod 42 moves through the needle stopper 34 to push against the head 62 to move the needle in a distal direction. One suitable rod 42 is a stainless steel rod. When the pushing force is removed from the plunger assembly 38, the spring 32 biases the head 62 of the needle 30 in a proximal direction until the head 62 runs up against (abuts) the needle stopper 34. The length of the needle stopper 34 is sized to ensure that the pointed distal end 60 of the needle 30 is retained in an unexposed position within the shaft 26 of the tool 20 until the plunger assembly 38 is activated. The spring 32 allows the surgeon to selectively move the needle 30 out of the shaft 26 by pushing on the button 40. Releasing the button 40 causes the spring 32 to bias the needle 30 back into the shaft 26.

In one embodiment, the spring is optional and is not included, and instead the needle 30 is integrated as one piece with the rod 42. The monolithic needle 30/rod 42 forms a plunger that is operated manually by the surgeon, where forward movement of the integrated needle 30/rod 42 delivers the suture through the glans penis and rearward retraction of the integrated needle 30/rod 42 retrieves the needle 30 back into the shaft 26.

Figure 2:
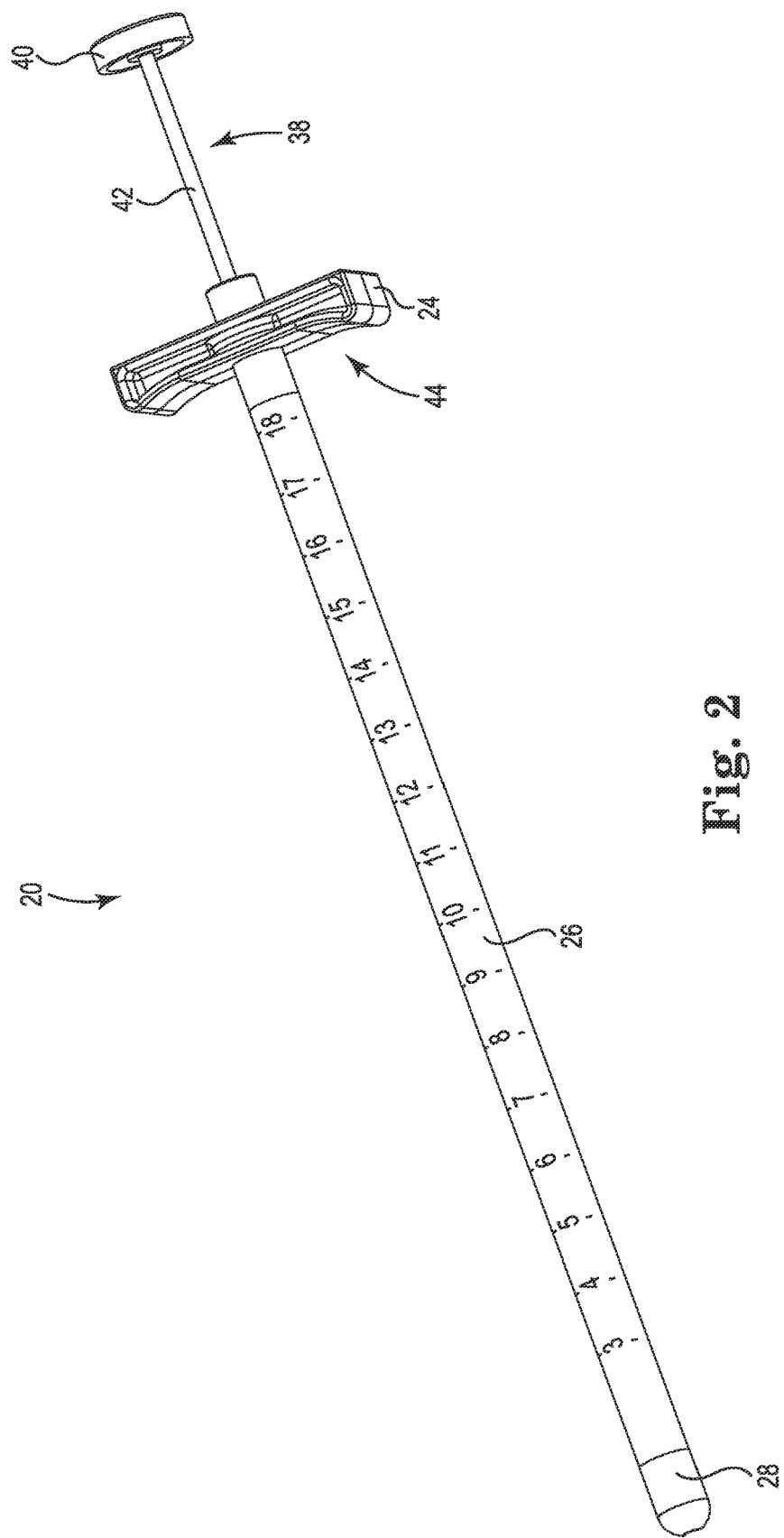
FIG. 2 is a perspective view of one embodiment of the tool illustrated in FIG. 1 as assembled.

FIG. 2 is a perspective view of the assembled tool 20. The tool 20 is illustrated at rest with the plunger assembly 38 in a neutral position and the pointed distal end 60 of the needle 30 (FIG. 1) retained in an unexposed position within the shaft 26. The button 40 and the rod 42 project a distance out of the shaft 26 for ergonomic placement relative to the thumb. The curve 44 of the handle 24 accommodates two or more fingers of the hand. When the thumb presses against the button 40, the rod 42 moves in a distal direction to drive the pointed distal end 60 of the needle 30 out of the tip 28.

FIG. 3 is a perspective view of a system 70 including the tool 20 and a penile prosthetic 72. The penile prosthetic 72 includes a penile implant 74 engaged with a suture 76. One suitable penile implant 74 includes the TITAN® Penile Implant available from Coloplast Corp., Minneapolis, Minn. In one embodiment, the suture 76 is provided as a single strand that is inserted through an eyelet 78 of the penile implant 74, where the single strand of the suture 76 is doubled to provide two thread portions 80. The tool 20 allows the needle 30 to be advanced in a distal direction for engagement with the two thread portions 80 of the suture 76. In a later step of the implantation procedure, the two thread portions 80 operate as a tow rope to pull the penile implant 74 into the dilated corpora cavernosum, as described below.

Figure 4A:
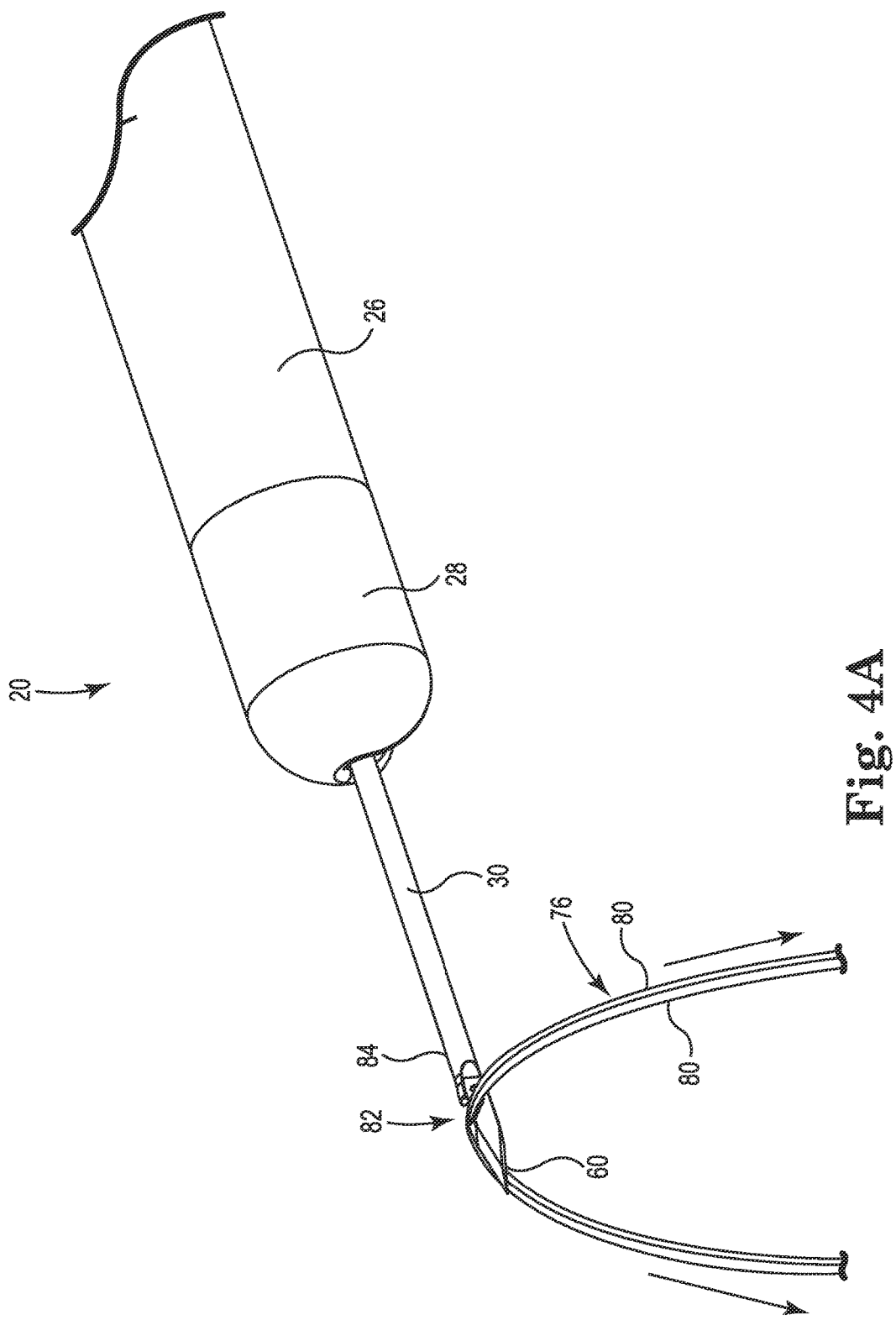

FIG. 4A is a perspective view of the needle 30 exposed from the distal tip 28 of the tool 20 and engaged with the two thread portions 80 of the suture 76. FIG. 4B is a perspective view of the needle 30 engaged with the suture 76. Pushing on the plunger assembly 38 (FIG. 2) exposes the pointed distal end 60 of the needle 30 out of the tip 28 of the tool 20. The surgeon, or one of the surgical staff, slides or drops the two thread portions 80 of the suture 76 into an open slot formed in the exposed portion of the needle 30. Retraction of the needle 30 to an unexposed location within the shaft 26 captures a portion of the two thread portions 80 of the suture 76 within the tool 20.

In one embodiment, the open slot is a notch 82 that is formed in an exterior surface 84 of the needle 30. The notch 82 provides an open area that allows the two thread portions 80 of the suture 76 to be easily and quickly engaged in the slot 82. The open slot of the notch 82 is distinguished from an eye of a needle in that a needle eye is a closed geometric opening. Dexterity and excellent vision is called upon to thread a small diameter suture through a small eye of a needle. In contrast, the open notch 82 allows the suture 76 to be simply placed into the notch 82 for immediate and positive engagement by the suture 76. The suture 76 is loaded into the notch 82 of the needle 30 by simply dropping the suture 76 onto the exterior surface 84 of the needle 30 and sliding the suture 76 along the needle 30 until it falls into the open notch 82. This approach reduces the amount of handling that is done with the needle 30 and are all much easier than threading a suture strand into an eyelet of a Keith needle. When the suture 76 is engaged with the notch 82, the two thread portions 80 dangle in a downward direction as shown in FIG. 4A FIG. 4B is a perspective view of the needle 30 illustrating the two thread portions 80 positively secured within the notch 82. The notch 82 provides an open slot and includes a projection 86 that projects over a portion of the open slot. The projection 86 operates to capture and retain the two thread portions 80 of the suture 76 when the needle 30 is pushed in a distal direction through tissue. The projection 86 operates to subsequently allow the suture 76 to exit the notch 82 when the needle retracts in a proximal direction.

In one embodiment, side portions 87 of the needle 30 are flattened to provide a relief space, which allows the suture 76 to have a lower profile when lying against the needle 30.

FIG. 4C is a front view of the needle 30. The side portions 87 located at the distal end portion of the needle 30 have a rectangular perimeter and the shaft of the needle 30 has a circular perimeter. The rectangular side portions 87 form a relief area to receive the suture 76 that is engaged in the notch 82. The side portions 87 provide the advantage of allowing the suture 76 to lie flat alongside the needle 30, thus providing a lower profile that experiences less resistance when passing through tissue.

FIG. 5A is a perspective view and FIG. 5B is an end view of the suture 76 captured by the tool 20. The needle 30 has been retracted in a proximal direction into an opening 88 of the tip 28 of the tool 20. When the needle 30 is retracted, the pointed end 60 of the needle 30 is maintained in a protected and unexposed position within the distal tip 28 of the tool 20.

FIG. 5B is an end view of the tip 28 of the tool 20. The bore 36 is formed longitudinally through the shaft 26 and the tip 28 and the needle 30 is disposed within the bore 36. The needle 30 and a portion of the suture 76 are retracted into the opening 88 of the tip 28.

The opening 88 is formed as a widened slot having angled sides. In one embodiment, the opening 88 is formed by walls 90 that diverge to provide an exterior arc 92 of the window, where a length of the exterior arc 92 is greater than a diameter of the bore 36. The walls 90 form opposing sides of the opening 88 and extend in a longitudinal direction to the arc 92, with the arc 92 being coincident with the side surface of the tip 28. The window of the opening 88 extends a radial depth measured from the bore 36 to the side surface of the tip 28 (see FIG. 5A). In one embodiment, the opening 88 is a widened slot that is coincident with the bore 36 and forms a space extending a longitudinal distance in a proximal direction away from a distal end of the tip 28 and a radial distance to the side surface of the tip 28. In one embodiment, the opening 88 is shaped like a space observatory window to provide clearance for both the needle 30 and the suture 76. The opening 88 provides the advantages of allowing the surgeon to visually check that the suture 76 is engaged by the needle 30 and provides a relief gap sized to accommodate the suture to reduce drag of the tissue against the suture 76.

FIG. 6 is a cross-sectional view of the tip 28 attached to the shaft 26 of the tool 20. The suture 76 is engaged in the notch 82 of the needle 30. The pointed end 60 of the needle 30 and a portion of the suture 76 are both retracted into the opening 88 formed by the wall 90 of the tip 28. In this configuration, the pointed end 60 of the needle 30 is not exposed to eliminate the possibility of an undesirable needle stick when handling the tool 20. In one embodiment, the tip 28 is fabricated of a transparent material to permit the healthcare worker to see through the tip 28 and view the status of the needle 30. In one embodiment, the tip 28 is fabricated of an opaque material.

In one embodiment, a shoulder 92 is provided within the tip 28 to capture a distal portion of the spring 32. The needle 30 and the spring 32 are both retained within the bore 36 that is formed in the shaft 26. The shoulder 92 provides a forward stop for the spring 32.

As noted above in FIG. 1, in some embodiments the spring 32 is optional and not employed, and instead the needle 30/rod 42 are integrated into a one piece plunger that is manually activated by the surgeon.

FIG. 7 is a perspective view of the needle 30 advanced in a distal direction out of the opening 88 to deliver the suture 76 outside of and beyond the tip 28 of the tool 20. In this delivery configuration and with reference to FIG. 2, the plunger assembly 38 has been moved in a distal direction to push the rod 42 against the head 62 of the needle 30 to move the pointed end 60 of the needle 30 out of the tip 28. The projection 86 pushes the suture 76 forward. Thus, during delivery of the suture 76, the distal motion of the needle 30 pulls/drags/pushes the suture 76 engaged in the notch 82 in a distal direction. During retraction of the needle 30 in the proximal direction the projection 86 allows the suture 76 to freely exit the open slot 82.

FIG. 8-FIG. 11 are schematic views of a procedure for implanting the penile implant 74 into a penis P.

The penis P is reclined against the torso. The groin area 100 of the patient is shaved, cleaned and suitably prepped with a surgical solution prior to draping with a sterile drape in accordance with the healthcare provider's procedures. A retraction device, such as those available from Lone Star Medical Products of Stafford, Tex., is placed around the penis P if so desired by the surgeon to establish the surgical field. A catheter 103 is inserted into the urethra U from the distal end (or glans) 104 of the penis P. Thereafter, the surgeon forms an incision to access the corpora cavernosa C1 and C2 of the penis.

Suitable examples of incisions for accessing the corpora cavernosa C1 and C2 include either an infrapubic incision or a transverse scrotal incision. The infrapubic incision is initiated between the umbilicus and the penis (i.e., above the penis), whereas the transverse scrotal incision is made across an upper portion of the patient's scrotum Sc.

As an example of the transverse scrotal approach, the surgeon forms a 2-3 cm transverse incision through the subcutaneous tissue of the median raphe of the upper scrotum Sc and dissects down through the Darto's fascia and Buck's fascia to expose the tunicae albuginea of the penis P. Thereafter, each corpora cavernosum C1 and C2 is exposed in a corporotomy where a small (approximately 1.5 cm) incision is formed to allow the surgeon to access and subsequently dilate the corpora cavernosa C1 and C2.

The surgeon typically will insert a blunt-ended scissors or other elongated tool to separate a portion of the spongiosum material to open a pathway for dilation and measurement of the corpora cavernosa C1, C2. After suitable dilation, the surgeon measures the length of the corpora cavernosa to determine the suitable size for the penile implant 74. In one approach, the surgeon ensures that the appropriately sized penile implant 74 has been selected by inserting the tool 20 into the corpora cavernosum C1 or C2 and using the indicia 50 to measure the proximal and distal length of each corpora cavernosum C1 and C2. For example, the tool 20 is inserted into one of the corpora cavernosa C1 or C2 forward in the distal penis toward the glans penis and the distal measurement is recorded by reading one of the marks 50. The tool 20 is then inserted into the same corpora cavernosa C1 or C2 rearward in the proximal penis toward the crus of the penis to record the proximal length of the corpora by reading one of the marks 50. The distal and proximal measurements would typically be made in reference to a "stay stitch" temporarily placed in the incision. The sum of the distal and the proximal measurements represent the length of that corpora cavernosum, and this information is used to select the size of the penile implant 74. This procedure is repeated for the other of the corpora cavernosa C1 or C2 to ensure the appropriately sized penile implant 74 has been selected for the companion corpora.

Figure 8:
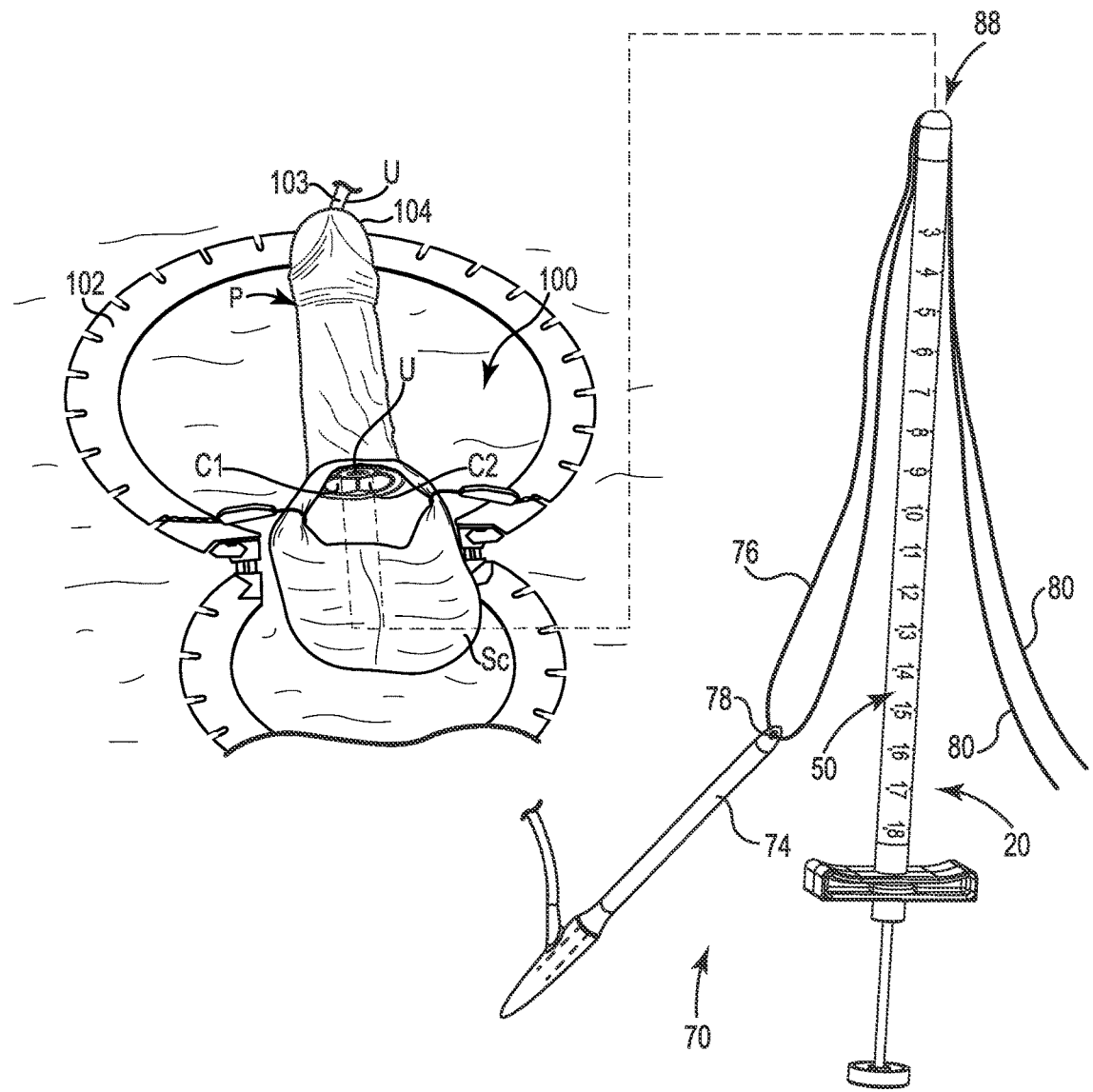
FIG. 8 is a schematic view of the system illustrated in FIG. 3 during implantation of the penile implant.

FIG. 8 illustrates the penis P prepped for surgery and the system 70 prepared for implantation of the penile implant 74 into the corpora cavernosum C2. The pointed end 60 of the needle 30 is protected in an unexposed position within the distal tip 28 of the tool 20. A portion of the suture 76 is engaged with the needle 30 and is retracted into the opening 88 of the tool 20.

Figure 9:
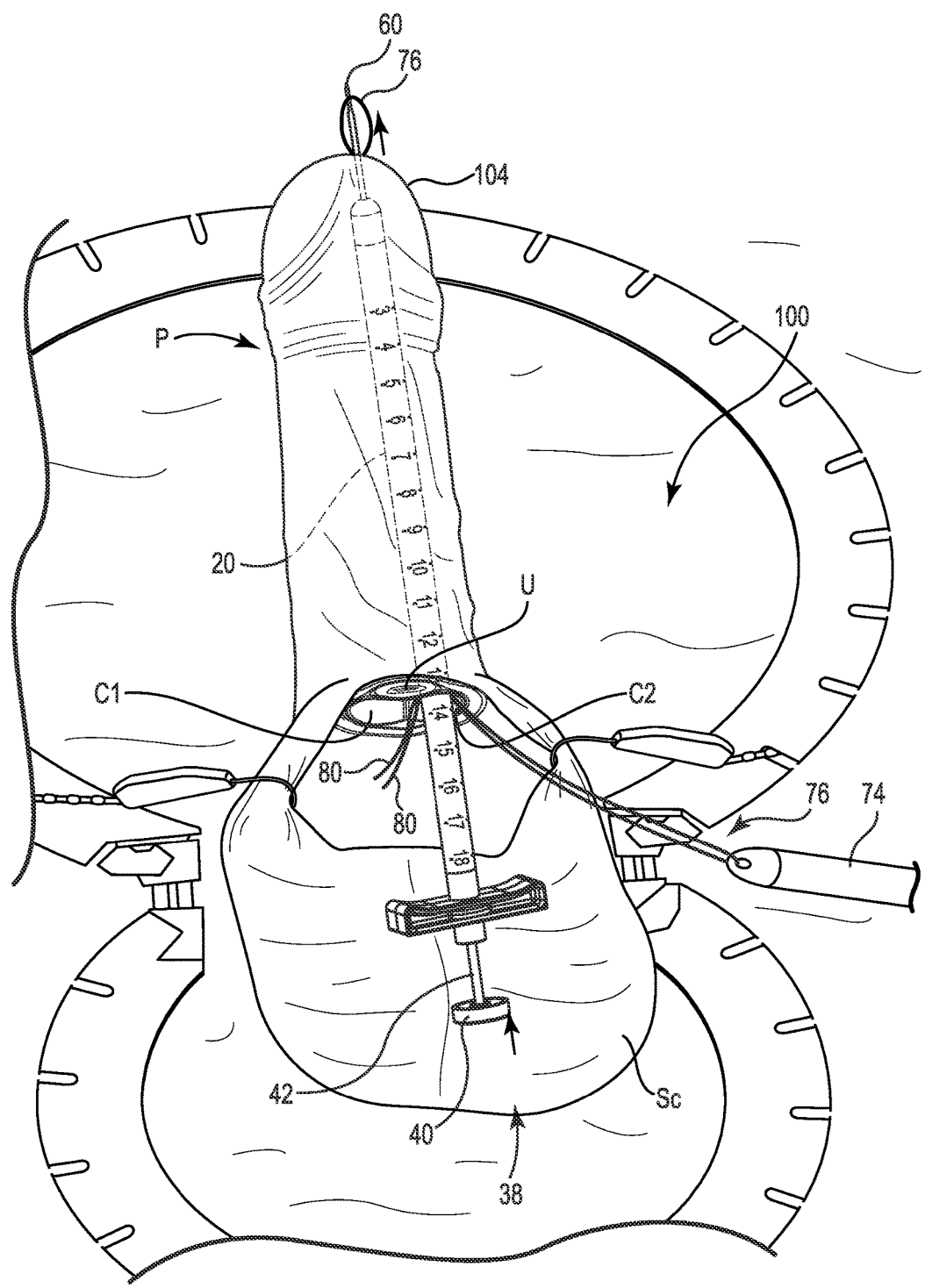
FIG. 9 is a schematic view of the system illustrated in FIG. 8 with the needle advancing a portion of the suture through a glans of the penis.

FIG. 9 is a schematic view of the tool 20 inserted into the corpora cavernosum C2. The penile implant 74 is outside of the penis P and is attached to the suture 76. The opposite free ends of the thread portions 80 of the suture 76 extend out of the corpora cavernosum C2 and are available for access by the surgeon. The surgeon, through experience, applies sufficient tension to the free ends 80 of the suture 76 to maintain the suture 76 alongside the shaft 26 of the tool 20. With reference to both FIG. 7 and FIG. 9, the button 40 of the plunger assembly 38 is moved in a distal direction to advance the pointed end 60 of the needle 30 and a portion of the suture 76 forward through the glans penis 104. The surgeon employs a forceps or other tool to grasp the portion of the suture 76 that is exposed exterior to the penis P. The button 40 is released and the pointed end 60 of the needle 30 is biased back into the shaft 26 of the tool 20. Upon retraction of the pointed end 60 of the needle 30 into the tool 20, the suture 76 is ejected out of the slot 82 formed through the exterior surface of the needle 30. The suture 76 will escape from the notch 82 when the needle is moved in the proximal direction, particularly as the suture 76 meets resistance from the glans penis 104.

Figure 10:
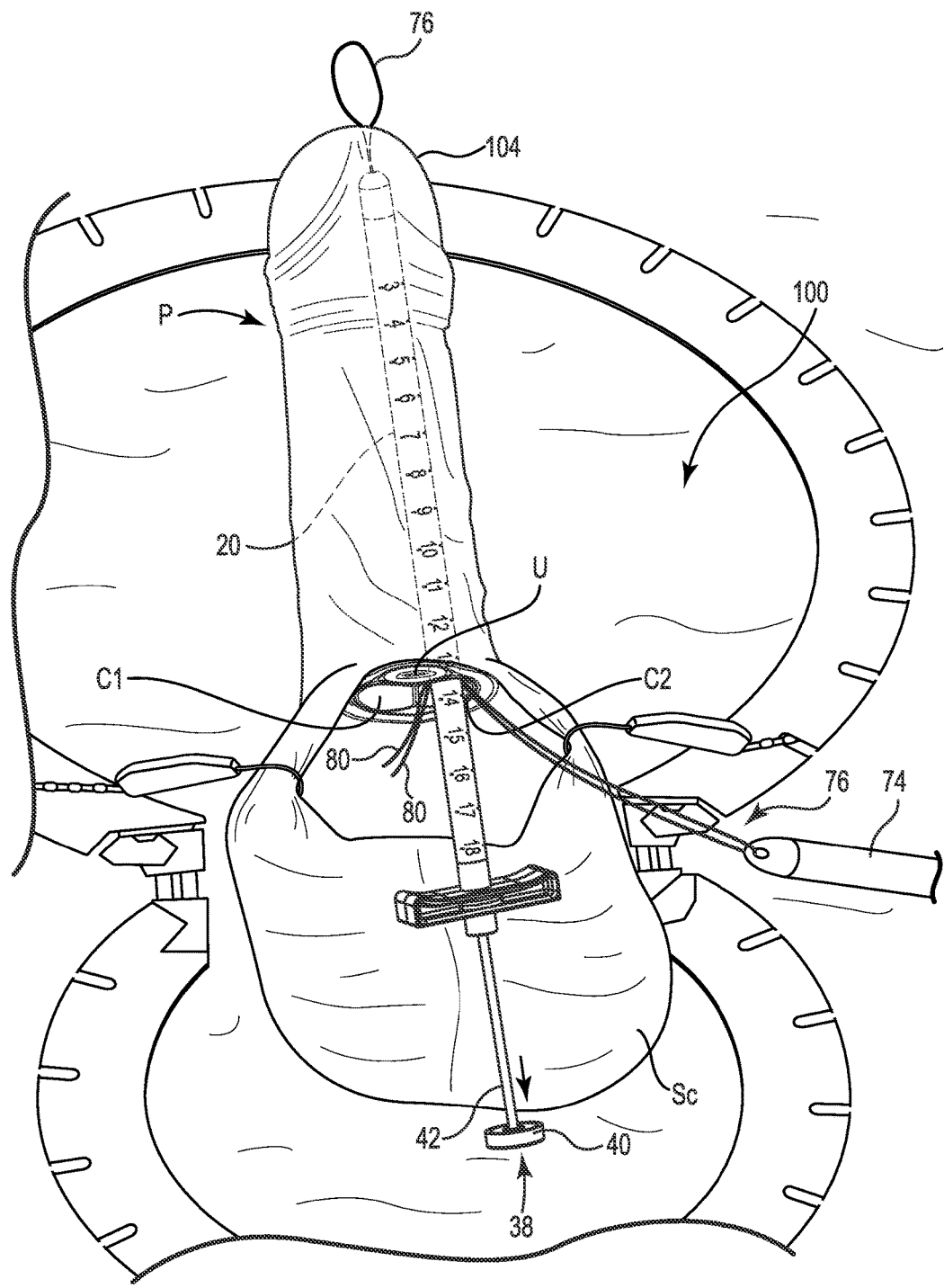
FIG. 10 is a schematic view of the system illustrated in FIG. 9 with the suture retained exterior to the penis and the needle retracted to an unexposed position within the tool.

FIG. 10 illustrates that the force applied to the plunger assembly 38 has been relaxed. The plunger assembly 38 has moved in a proximal direction, and the spring 32 biased the pointed end 60 of the needle 30 into the protected, unexposed position within the tip 28. The exposed part of the suture 76 is displaced from the notch 82 of the needle 30 and remains outside the glans penis 104. The needle 30 has been safely retracted into the tip 28 of the tool 20. The tool 20 may now be removed from the corpora cavernosum C2.

Figure 11:
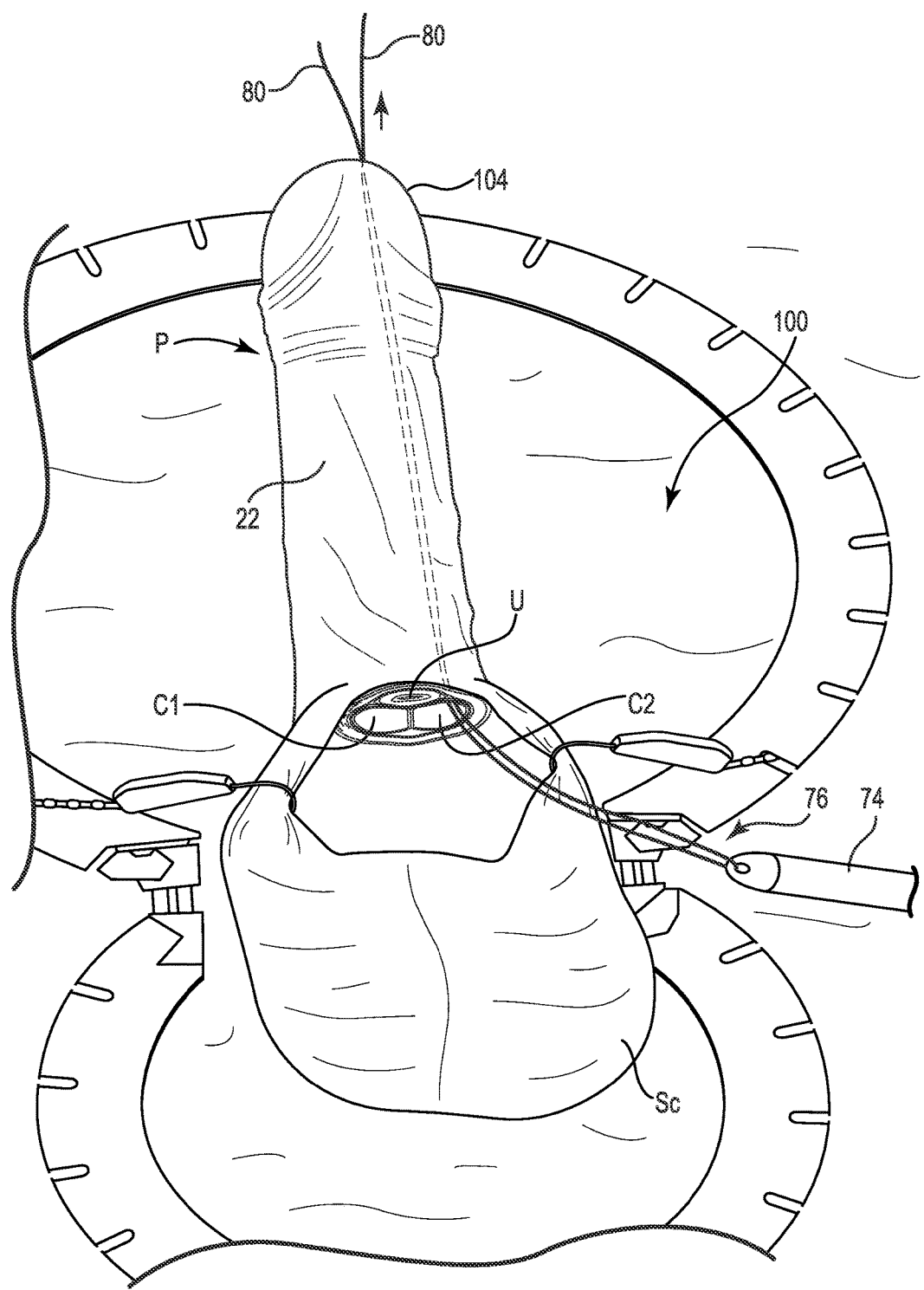
FIG. 11 is a schematic view of the penile implant being towed by the suture to a location within a dilated corpora cavernosum of the penis.

FIG. 11 illustrates that the suture 76 is employed to tow the penile implant 74 distally into the corpora cavernosum C2 up to the glans penis. The implant 76 is placed in the corpora cavernosum and the suture 76 is removed from the implant 74.

The proximal end of the penile implant 74 is suitably implanted proximately into the crus penis.

A second penile prosthetic is implanted in the corpora cavernosum C1 following the steps described above for implantation of the penile implant 74 the corpora cavernosum C2.

The steps of one acceptable method of using the tool 20 include:

Press plunger assembly until needle sticks out approximately 1 inch; hold this position of plunger;

Place tow sutures into the needle slot/open notch;

Fold sutures down towards floor and slowly release the plunger to allow needle to retract;

Pull sutures toward the handle and clasp the sutures against shaft of the tool;

Insert the tool fully into a dilated corpora;

Press the plunger until the point of the needle fully protrudes through glans;

Allow the needle to retract slightly and then grasp tow suture loop with clamp as the suture is ejected out of the needle slot/open notch;

Allow the needle to fully retract and then remove the tool from the corpora while continuing to grasp tow sutures;

Pull on the tow sutures to bring the implant fully into the corpus, then pull the suture out of the implant and out of the corpus;

Repeat for the second implant in the second corpus.

Sliding the suture into the slot formed through the exterior surface of the needle and securing the suture in the slot with a projection formed to project over a portion of the slot provides the advantage of quickly and easily loading suture into the needle.

Sliding the suture into an open slot formed through the exterior surface of the needle has the advantage of ensuring that the suture is engaged with the needle without having to squint for a small needle eyelet.

Retracting the distal end of the needle and the portion of the suture into an opening formed in a distal tip of the tool, with the opening formed by a wall that extends from the bore of the tool to a side exterior surface of the distal tip of the tool has the advantage of reducing the possibility of a sharp needle stick and grasping the suture so that it does not slide out of engagement with the needle.

Exposing a sharp pointed distal end of the needle out of a tip of the tool and retracting the sharp pointed distal end of the needle back into an unexposed position within the tip of the tool has the advantage of being able to control whether the sharp point of the needle is exposed.

Biasing a sharp pointed distal end of the needle into an unexposed position within a tip of the tool has the advantage of protecting the surgical staff from sharp needle sticks.

Grasping the portion of the suture exterior to the glans of the penis and biasing a sharp pointed distal end of the needle into an unexposed position within a tip of the tool has the advantage of moving the needle out of the way without having to handle the needle. This is a noted advantage over the process of pulling the Keith needle through the glans penis, disengaging the Keith needle from the suture, and disposing of the sharp Keith needle.

Inserting the shaft of the tool into the corpora cavernosum of the penis and measuring a length of the corpora cavernosum of the penis has the advantage of providing multiple modes of utility with one tool, including using the tool as a measuring device.

Retracting the distal end of the needle into the bore of the tool and displacing the suture out from the slot formed through the exterior surface of the needle has the advantage of disengaging the suture from the needle without having to handle the needle.

Retracting the distal end of the needle into the bore of the tool by passing the needle through the glans of the penis and pushing the suture out from the slot formed through the exterior surface of the needle with the glans of the penis also has the advantage of disengaging the suture from the needle without having to handle the needle.

Evaluations were performed on other open notched needle shapes configured to allow the suture to be easily engaged into the notch and displaceable out of the notch.

Figure 12:
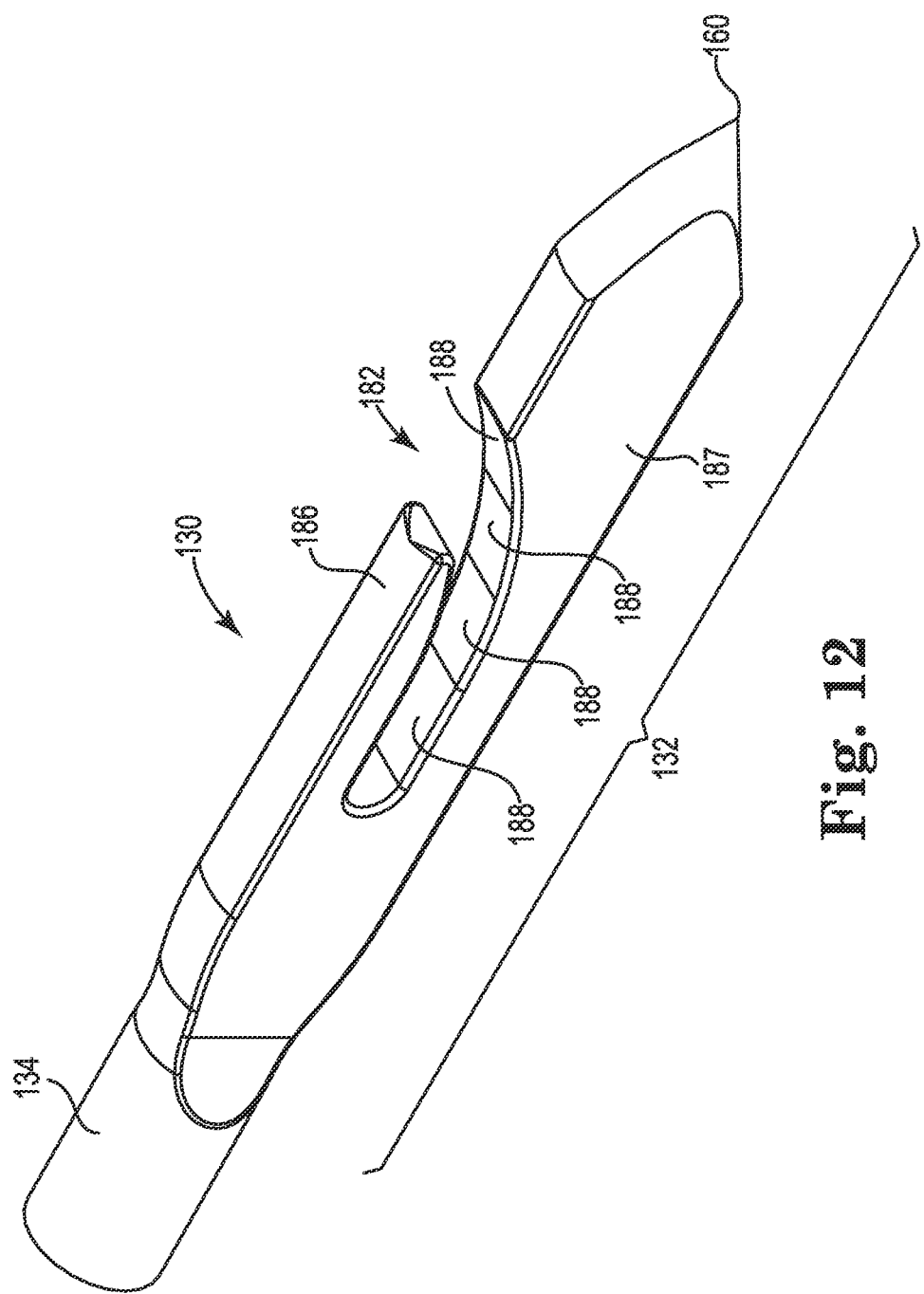
FIG. 12 is a perspective view of one embodiment of a needle of the tool illustrated in FIG. 2.

FIG. 12 is a perspective view of one embodiment of a needle 130 of the tool 20. The needle 130 includes a distal end portion 132 and a pointed distal end 160 both extending from a circular shaft 134. An open notch 182 is formed through an exterior surface of the needle 130 and a projection 186 is provided to retain the suture as it is pushed through tissue. In one embodiment, the distal end portion 132 includes relief zone(s) 187 formed as one or more flat surfaces on one or both sides of the needle shaft 134. The open notch 182 is longer in a longitudinal direction than the notch 82 described above and includes articulated sections 188. The articulated sections 188 provide a ramp that allows the suture to slide into and out of the notch 182.

Figure 13:
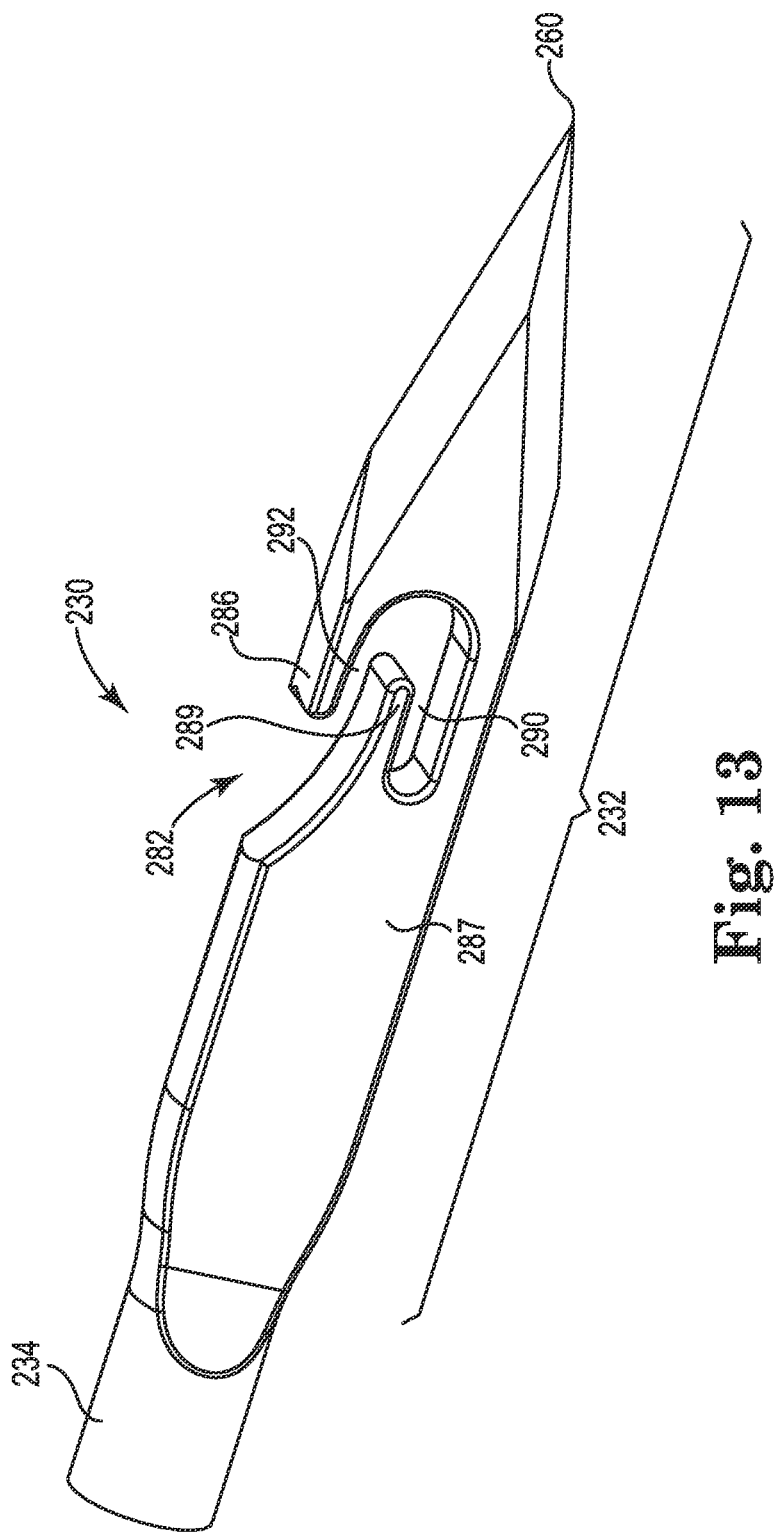
FIG. 13 is a perspective view of one embodiment of a needle of the tool illustrated in FIG. 2.

FIG. 13 is a perspective view of one embodiment of a needle 230 of the tool 20. The needle 230 includes a distal end portion 232 and a pointed distal end 260 both extending from a circular shaft 234. An open notch 282 is formed through an exterior surface of the needle 230. An exterior projection 286 is provided at an outer perimeter of the notch 282 and an interior projection 289 is provided with an outer periphery of the notch 282. The projections 286, 289 are provided to retain the suture as it is pushed through tissue. In one embodiment, the distal end portion 232 includes relief zone(s) 287 formed as one or more flat surfaces on one or both sides of the needle shaft 234. The open notch 282 is C-shaped with the interior projection 289 separating the notch 282 into a lower compartment 290 and an upper compartment 292.

Figure 14:
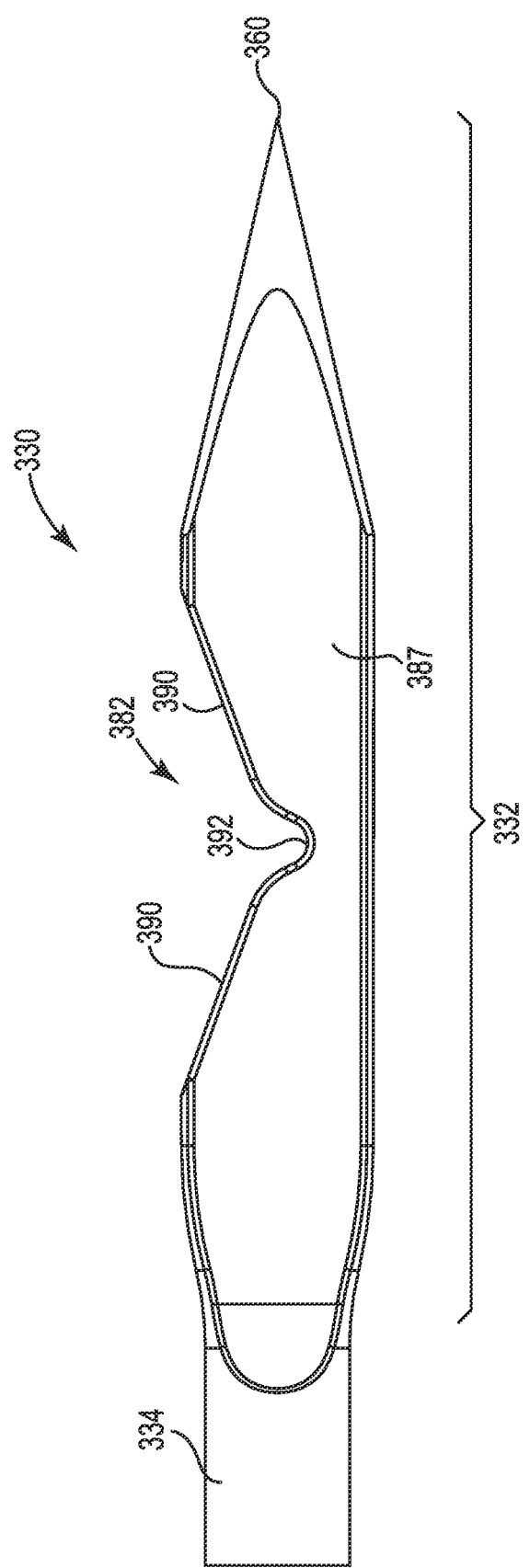
FIG. 14 is a perspective view of one embodiment of a needle of the tool illustrated in FIG. 2.

FIG. 14 is a perspective view of one embodiment of a needle 330 of the tool 20. The needle 330 includes a distal end portion 332 and a pointed distal end 360 both extending from a circular shaft 334. An open notch 382 is formed through an exterior surface of the needle 330. The open notch 382 includes a funnel shaped set of walls 390 that terminate at a well 392. In one embodiment, the distal end portion 332 includes relief zone(s) 387 formed as one or more flat surfaces on one or both sides of the needle shaft 334. The open notch 382 is V-shaped and the well 392 readily receives the suture during the suture loading step.

Figure 15:
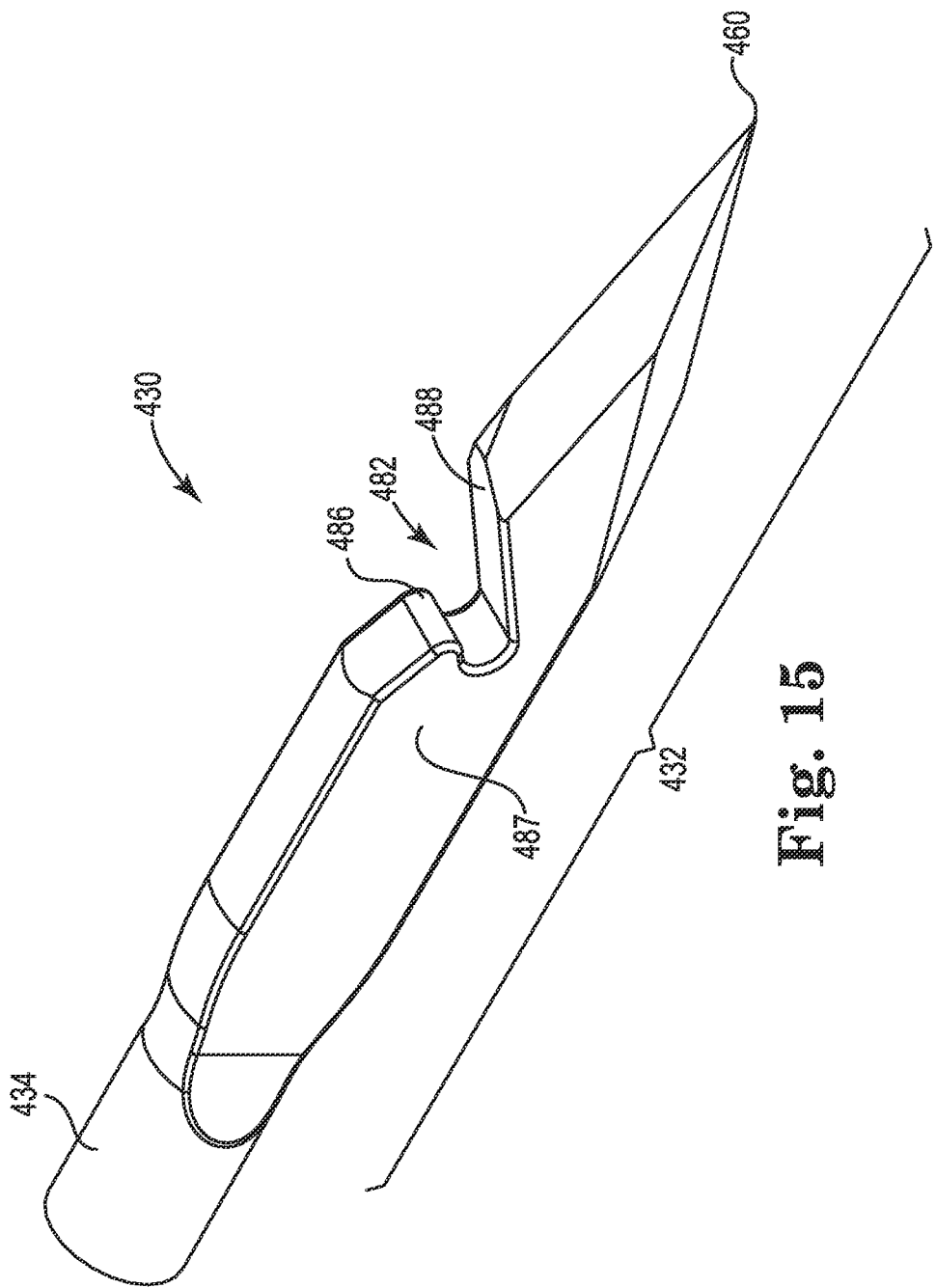
FIG. 15 is a perspective view of one embodiment of a needle of the tool illustrated in FIG. 2.

FIG. 15 is a perspective view of one embodiment of a needle 430 of the tool 20. The needle 430 includes a distal end portion 432 and a pointed distal end 460 both extending from a circular shaft 434. An open notch 482 is formed through an exterior surface of the needle 430 and a projection 486 is provided to retain the suture as it is pushed through tissue. In one embodiment, the distal end portion 432 includes relief zone(s) 487 formed as one or more flat surfaces on one or both sides of the needle shaft 434. The open notch 482 is shorter in a longitudinal direction than the notch 82 described above and includes a linear ramp 488 at an entrance of the notch 482.

FIG. 16 is a perspective view of one embodiment of a needle 530 of the tool 20. The needle 530 includes a distal end portion 532 and a pointed distal end 560 both extending from a circular shaft 534. An open notch 582 is formed through an exterior surface of the needle 530 and a projection 586 is provided to retain the suture as it is pushed through tissue. In one embodiment, the distal end portion 532 includes relief zone(s) 587 formed as one or more flat surfaces on one or both sides of the needle shaft 534. The open notch 582 is deeper in a radial direction than the notch 82 described above and includes a linear ramp 588 that connects between a planar well 592 at a bottom of the notch 582 and an entrance of the notch 582.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A method of implanting a penile prosthetic, the method comprising:
   advancing a distal end of a needle out of a bore of a tool;
   capturing a suture in a slot formed through an exterior surface of the needle, the suture engaged with a penile implant, wherein the needle includes a projection that projects over a proximal portion of the slot with a distal portion of the slot including an entrance for receiving the suture and a ramp that connects between a well at a bottom of the slot and a distal edge of the entrance;
   retracting the distal end of the needle and a portion of the suture into the bore of the tool;
   inserting a shaft of the tool into a corpora cavernosum of a penis and forcing the distal end of the needle and the portion of the suture out of the bore of the tool and through a glans of the penis;
   retracting the distal end of the needle into the bore of the tool and retaining the portion of the suture exterior to the glans of the penis;
   removing the shaft of the tool from the corpora cavernosum of the penis; and
   pulling on the suture and pulling the penile implant into the corpora cavernosum of the penis.

2. The method of claim 1, comprising sliding the suture into the slot formed through the exterior surface of the needle.

3. The method of claim 1, comprising retracting the distal end of the needle and the portion of the suture into an opening of the bore formed in a distal tip of the tool, with the opening formed by a wall that extends from the bore of the tool to a side exterior surface of the distal tip of the tool.

4. The method of claim 1, comprising exposing a sharp pointed distal end of the needle out of a tip of the tool and retracting the sharp pointed distal end of the needle back into an unexposed position within the tip of the tool.

5. The method of claim 1, comprising biasing a sharp pointed distal end of the needle into an unexposed position within a tip of the tool.

6. The method of claim 1, comprising retracting the distal end of the needle into the bore of the tool by biasing the needle in a proximal direction with a spring.

7. The method of claim 1, comprising grasping the portion of the suture exterior to the glans of the penis and biasing a sharp pointed distal end of the needle into an unexposed position within a tip of the tool.

8. The method of claim 1, comprising inserting the shaft of the tool into the corpora cavernosum of the penis and measuring a length of the corpora cavernosum of the penis.

9. The method of claim 1, comprising retracting the distal end of the needle into the bore of the tool and displacing the suture out from the slot formed through the exterior surface of the needle.

10. A method of implanting a penile prosthetic, the method comprising:
　　advancing a distal end of a needle out of a bore of a tool;
　　capturing a suture in a slot formed through an exterior surface of the needle, the suture engaged with a penile implant;
　　retracting the distal end of the needle and a portion of the suture into the bore of the tool;
　　inserting a shaft of the tool into a corpora cavernosum of a penis and forcing the distal end of the needle and the portion of the suture out of the bore of the tool and through a glans of the penis;
　　retracting the distal end of the needle into the bore of the tool by passing the needle through the glans of the penis and ejecting the suture out from the slot formed through the exterior surface of the needle with the glans of the penis and retaining the portion of the suture exterior to the glans of the penis;
　　removing the shaft of the tool from the corpora cavernosum of the penis; and
　　pulling on the suture and pulling the penile implant into the corpora cavernosum of the penis.

11. A method of implanting a penile implant, the method comprising:
　　exposing a pointed distal end of a needle out of an opening of a tool;
　　dropping a suture into an open notch formed in an exterior surface of the needle, with the suture engaged with the penile implant, wherein the needle includes a projection that projects over a proximal portion of the open notch with a distal portion of the open notch including an entrance for receiving the suture and a ramp that connects between a well at a bottom of the open notch and a distal edge of the entrance;
　　biasing the pointed distal end of the needle into an unexposed position within the opening of the tool and trapping a portion of the suture within a distal tip of the tool;
　　inserting the distal tip of the tool into a corpora cavernosum of a penis;
　　pushing the pointed distal end of the open notch of the needle through a glans of the penis;
　　delivering the portion of the suture through the glans of the penis with the open notch of the needle;
　　biasing the pointed distal end of the needle back to the unexposed position within the opening of the tool and retaining the portion of the suture exterior to the penis;
　　removing the distal tip of the tool from the corpora cavernosum of the penis; and
　　pulling on the portion of the suture exterior to the penis to pull the penile implant into the corpora cavernosum of the penis.

12. The method of claim 11, comprising biasing the pointed distal end of the needle back to the unexposed position within the opening of the tool with a spring and ejecting the suture out of the open notch formed in the exterior surface of the needle.

13. A method comprising:
　　inserting a shaft of a tool into a corpora cavernosum of a penis, wherein the tool comprises:
　　　　the shaft;
　　　　a needle within the shaft, the needle including a pointed distal end, a notch formed in an exterior surface of the needle, a projection that projects over a proximal portion of the notch with a distal portion of the notch including an entrance, and a ramp that connects between a well at a bottom of the notch and a distal edge of the entrance; and
　　　　a suture passing through the notch and engaged with a penile implant;
　　pushing the pointed distal end of the needle and a portion of the suture beyond a distal end of the shaft and through a glans of the penis to a location exterior of the penis;
　　retracting the pointed distal end of the needle back towards the distal end of the shaft;
　　ejecting the portion of the suture out of the notch formed in the exterior surface of the needle, and retaining the portion of the suture exterior to the penis; and
　　removing the shaft of the tool from the corpora cavernosum of the penis.

* * * * *